United States Patent [19]

Matsuda et al.

[11] 4,269,765

[45] May 26, 1981

[54] IMMUNE SERUM FOR DIAGNOSIS OF CANCER AND PREPARATION THEREOF

[75] Inventors: Yoshiji Matsuda; Keiji Tamura, both of Sendai; Hiroaki Motoki, Koganei; Fumio Kitame; Nakao Ishida, both of Sendai, all of Japan

[73] Assignees: Kabushiki Kaisha Saikin Kagaku Kenkyujo, Miyagi; Kabushiki Kaisha Kayaku Kosei Bushitsu Kenkyujo, Tokyo, both of Japan

[21] Appl. No.: 891,645

[22] Filed: Mar. 30, 1978

[30] Foreign Application Priority Data

Jun. 16, 1977 [JP] Japan ................................. 52-71349

[51] Int. Cl.³ ..................... A61K 39/00; A61K 39/44; C07G 7/00; G01N 33/54
[52] U.S. Cl. ................. 260/112 B; 23/230 B; 260/112 R; 424/105; 424/1; 424/88; 424/95; 424/100; 424/101; 424/8; 424/12; 424/85
[58] Field of Search ............. 424/1, 8, 12, 85, 88, 424/95, 100, 101, 105; 260/112 R, 112 B; 23/230 B

[56] References Cited

U.S. PATENT DOCUMENTS 3,819,822  6/1974  Nagai ..................................... 424/12

OTHER PUBLICATIONS

Motoki, Gann, vol. 66, 1975 pp. 569-572.
Motoki, Chem. Abs., vol. 84, 1976 Ab. No. 29024j.
Purves, South African Med. J. vol. 42, 1968, pp. 1138-1141.
Kwapinski, Methodology of Immunochem. & Immunol. Res., Wiley-Intersci. NY 1972.
Matsuda, 35th General Meeting of Japanese Cancer Asso., 1976, Ab. No. 187.

Primary Examiner—Anna P. Fagelson
Attorney, Agent, or Firm—Scrivener, Clarke, Scrivener and Johnson

[57] ABSTRACT

The present invention provides a method for the preparation of a specific immune serum by immunizing IAP in animals other than humans and absorbing the thus obtained serum with normal human serum.

4 Claims, 3 Drawing Figures

IMMUNE SERUM FOR DIAGNOSIS OF CANCER AND PREPARATION THEREOF

DETAILED DESCRIPTION OF THE INVENTION

The present invention relates to a method for the preparation of a specific immune serum effective in the diagnosis of cancers.

The conventional immunological or chemical diagnoses of cancers is such that serum proteins, serum enzymes or hormones are assayed or quantitated. Patients suffering from cancer are usually characterized by the appearance, or the increase in quantity of $\alpha_1$-globulin, $\alpha_2$-globulin and $\beta$-globulin in their sera. These globulins contain immunoregulatory $\alpha_2$-globulin (IRA), glycoprotein, $\alpha_1$-fetoprotein, carcinoembryonic antigen (CEA), $\alpha_2$-macroglobulin and $\alpha_1$-antitrypsin. The appearance of $\alpha_1$-fetoprotein and CEA in the srum is especially remarkable. The former appears at the rate of 50 to 80% in the sera of patients suffering from idiopathic liver cancer while the latter appears in 70 to 90% of the sera from patients suffering from colorectal carcinoma.

At the 35th general meeting of the Japanese Cancer Association (1976) MATSUDA et al. reported that an acidic protein with an isoelectric point of 3.0 to 3.4 and a molecular weight of 59,000 and containing a small amount of sugar existed in the sera or periotoneal fluid of patients suffering from cancers of the stomach, colon, bladder, and lymphosarcoma and that this protein may be separated and purified by negative ion-exchange chromatography and thin layer gel electrofocusing. In subsequent studies the inventors found that an acidic protein with an iso-electric point of 2.9 to 3.3 and a molecular weight of about 59,000 which can be separated by negative ion-exchange chromatography from serum and other body fluids of cancer patients is active in suppressing immunity, therefore it is called immunosuppressive acidic protein and will be referred to as "IAP".

Therefore the inventors made extensive studies and experiments to measure the quantitative increase in IAP and other agents used in the diagnosis of cancer and the patient's condition after operation. As a result, the inventors found that an immune serum or antiserum prepared by the injection of IAP into animals other than humans reacted with IAP causing an antigen-antibody reaction. Thus quantitative measurement of IAP became possible without the use of complex chemical analysis and expensive instruments and equipment.

PHYSICAL AND CHEMICAL CHARACTERISTICS OF IAP

The starting material, or IAP is prepared by subjecting serum, peritoneal or thoracic fluid, urine, other body fluids from cancer patients or the liquid extracted from the placentas of healthy humans to negative ion-exchange chromatography and collecting the protein with an isoelectric point of 2.9 to 3.3. The substance thus obtained, exhibits the following properties:

(1) Molecular weight: about 59,000 (measured by the electrophoresis with 7.5% polyacrylamide gel containing sodium dodecyl sulfate)
(2) Apperance: white powder
(3) Solubility: Soluble in water, in 0.01M phosphate buffered saline. Insoluble in methanol, ethanol, butanol, acetone, ethyl acetate and chloroform.
(4) Isoelectric point: pI 2.9–3.3 (by thin layer gel electrofocusing)
(5) Amino acid composition: Treatment of 1 mg of the substance to hydrolysis in 2 ml of 6 N hydrochloric acid at 120° C. for 15 hours results in a positive reaction with ninhydrin thereby indicating the presence of amino acids.
(6) Color reactions: Positive to von Euler's, Ehrlich's, Buret's and Molisch's reactions, but negative to ferric chloride and lieberman's reactions.
(7) Decomposition point: 265° C.
(8) Infrared absorption spectrum (with 0.5% KBr): See FIG. 1 showing maxima at 3300 cm$^{-1}$, 2940 cm$^{-1}$, 2340 cm$^{-1}$, 1650 cm$^{-1}$, 1540 cm$^{-1}$, 1440 cm$^{-1}$, 1400 cm$^{-1}$, 1240 cm$^{-1}$, 1060 cm$^{-1}$,
(9) Ultraviolet absorption spectrum (dissolved in distilled water to 0.02%.): See FIG. 2 showing $\lambda$max=280 nm
(10) Stability:

| Conditions | 2 mg of acidic protein was dissolved in 10 ml of phosphate buffered saline (pH = 7.2). |
|---|---|
| 100° C., 5 minutes | inactivated |
| 60° C., 30 minutes | inactivated |
| 4° C., 24 hours | stable |
| 18 ~ 20° C., 2 days | stable |
| −20° C., 7 days | stable |

PREPARATION OF THE SPECIFIC IMMUNE SERUM (ANTI-IAP-SERUM)

In order to carry out the present invention, the serum, peritoneal or thoracic fluid, urine, other body fluids from cancer patients or the liquid extracted from placentas of healthy humans containing IAP or purified IAP, were added to Freund's complete adjuvant (a product of Difco Co.,) emulsified and injected subsutaneously into an animal e.g. rabbit, sheep, horse or cow. Injections were repeated at suitable intervals, and the animals bled when the antibody concentrations had reached a predetermined level. This immune serum was absorbed with normal human serum or insoluble human serum prepared by the treatment of normal human serum with glutaraldehyde. That is, the immune serum was added to the normal human serum or the normal human insoluble serum and incubated at 37° C. for 30 minutes to two hours. The sediment that formed was separated by centrifugation, and the supernatant was added to the same amount of fresh normal human serum and stood at 4° C. overnight. The sediment was again separated by centrifugation, and the supernatant was taken as the desired specific immune serum.

This immune serum was then subjected to the antigen-antibody reaction with IAP extracted from the cancer patient as described later in Example 1. Various methods were used such as double immunodiffusion, single immunodiffusion, immunoelectrophoresis, antigen-antibody crossing immunoelectrophoresis, antigen-antibody countercurrent immunoelectrophoresis, rocket electrophoresis, sensitized blood cell agglutination, radio-immuno assay, enzyme immunity assay etc., in order to make quantitative measurements of the IAP content in human serum, peritoneal or thoracic fluid, or other body fluids in the diagnosis of cancer.

The present invention will now be described in greater detail with reference to some examples taken in conjunction with the accompanying drawings, in which.

THE EXTRACTION AND PURIFICATION OF IAP

Reference Example 1

Figure 1:
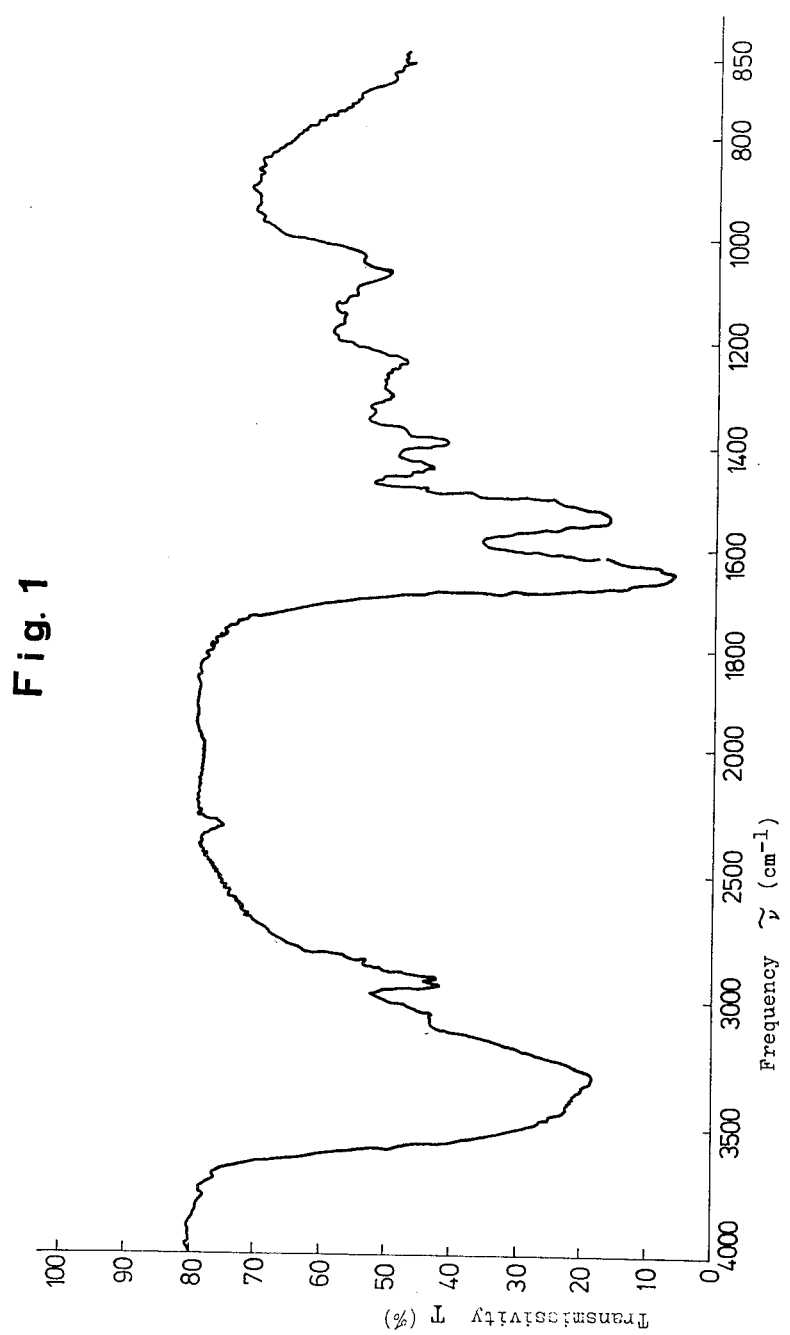
FIG. 1 shows the infrared absorption spectrum of IAP.
Figure 2:
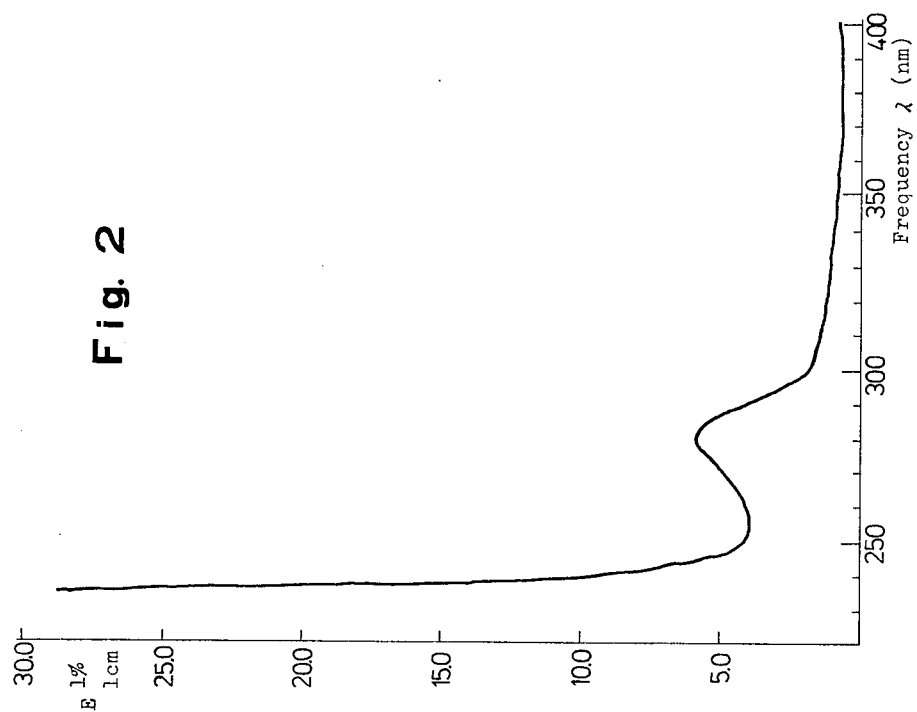
FIG. 2 shows the ultraviolet absorption spectrum of IAP.

10 ml of peritoneal fluid containing IAP extracted from a patient suffering from stomach cancer was adjusted to pH 5.5 with acetic acid and absorbed into diethylaminoethyl (DEAE) cellulose (a product of Wattmann Co.) that had been equilibrated with 0.02 M acetate buffer, pH 5.5. The absorbed peritoneal fluid was dissolved with an ion gradient of 0.02 to 0.5 M acetate buffer and fractionated into four. It was confirmed that the acidic protein was eluted in the third fraction by thin layer gel electrofocusing, pH from 2.5 to 6.0. As this fraction contained other substances, it was subjected to dialysis in 0.02 M acetate buffer and then absorbed again in DEAE cellulose equilibrated with 0.04 M acetate buffer, pH 5.1. Next the absorbed substance was subjected to ion gradient chromatography with 0.04 to 0.4 M acetate buffer, pH 5.1 and fractionated into three. IAP was shown to be eluted in the second fraction by thin layer gel electrofocusing. It was desalted, frozen and dried. 27.2 mg of white IAP powder was obtained.

Reference Example 2

Following the procedures of Reference Example 1, 20 mg of the third fraction obtained by the first chromatographic process was subjected to isoelectric column electrophoresis from pH 2.5 to 6.0) so that IAP at pH 2.9 to 3.3 was obtained as a single substance. This fraction was further subjected to dialysis to remove sucrose and the carrier ampholite. It was then frozen and dried. 4 mg of white purified IAP powder was obtained.

Reference Example 3

10 ml of serum from a human suffering from stomach cancer was diluted by 50% with phosphate buffered saline, and 4 mls of the diluted solution poured into each of five containers. Ammonium sulfate was added to make 30, 40, 50, 60 and 70% saturated solutions, respectively. After standing for one hour at 4° C., the mixtures were centrifuged for ten minutes at $10,000 \times g$. The pellets were each dissolved in 5 ml of 0.14 M phosphate buffered saline, and subjected to dialysis and desalting. The supernatants were also dialysed with the phosphate buffered saline and desalted. The desalted specimens were subjected to thin layer gel electrofocusing. It was found that the IAP with an isoelectric point of 2.9 to 3.3 was not precipitated from the specimens saturated with less than 50% ammonium sulfate, whereas 100 mg and 130 mg of IAP were obtained from the 60% and 70% ammonium sulfate saturated solution, respectively.

Reference Example 4

10 placentas of humans were finely divided and added to 1 l of 0.1 M sodium chloride solution and mixed for a short time. The extracted placental blood was centrifuged and a 2 l supernatant was obtained. Following the procedures of Reference Example 1, 1.6 grams of IAP with an isoelectric point of 2.9 to 3.3 was obtained.

Reference Example 5

1,000 ml of urine containing IAP from a patient suffering from cancer was subjected to dialysis with distilled water and frozen and dried. The frozen substance was finely divided and dissolved in 50 ml of 1/15 M phosphate buffered saline (pH=7.4).

The solution was poured onto a Sephadex G-75 (a product of Pharmacia Co.) column, equilibrated with the same buffer solution. By the thin layer gel electrofocusing, pH 2.5 to 6.0, it was found that the IAP was eluted in the first protein fraction. This fraction was absorbed with DEAE cellulose which had been equilibrated with 0.02 M acetate buffer, pH 4.0, and was extracted by one step elution with a 0.02 to 0.4 M acetate buffer, pH 4.0. The IAP was concentrated between 0.2 to 0.4 M acetate buffer. These fractions were desalted, frozen and dried, and 10 mg of protein was obtained as purified IAP by isoelectric point column electrophoresis, pH from 2.9 to 3.3.

EXAMPLE 1

IAP obtained by the process described in Reference Example 2 was proportioned with saline to 4 mg/ml, and 0.5 ml of this solution was added to an equal amount of Freund's complete adjuvant and emulsified. The mixture was injected subcutaneously at several points along the back of a rabbit weighing about 2 kg. Two weeks later, 1 ml of the same IAP emulsified mixture was injected, and two weeks after this, the same amount was again injected. Ten days from the last injection the rabbit was bled, and the serum was separated and inactivated at 56° C. for 30 minutes. Sodium azide was added to make a concentration of 0.05% in order to sterilize the sample. 1 ml of this prepared immune serum was added to normal human insoluble serum and incubated for two hours at 37° C. It was then centrifuged for 30 minutes at 4° C. at 5,000 rpm. The supernatant was again added to the same amount of normal human insoluble serum and stored at 4° C. overnight. This was centrifuged again to obtain the specific immune serum The specific reaction of the IAP antibodies in the prepared immune serum was confirmed by double immunodiffusion (microouchterlony) method and immunoelectrophoresis with an antigen derived from the serum or peritoneal fluid of a patient suffering from cancer. Furthermore, this immune serum did not react with healty human serum in the same test. Thus, it was confirmed that the immune serum contained no antibodies other than IAP antibodies.

EXAMPLE 2

Agar-gel (or refined agar) was added to 1/15 M phosphate buffered saline (pH=7.4) in such a way that the concentration of the former was 1.2% (1.0%). The mixture was heated and poured into a container so that a gel sheet 1.5 mm in thickness and with a flat surface was formed. Wells with a diameter of 3 mm were formed and spaced apart about 3 mm from each other.

The antiserum in accordance with the present invention, the serum to be assayed and the reference serum containing IAP were added so that they completely filled these wells and were then left for 24 hours at room temperature. The formation of precipitate lines between the immune serum and the serum under examination were checked, and those having such lines were classified as being positive for IAP. The results are shown in Table I below.

TABLE I

| Subject | Number tested | Number of positive cases |
| --- | --- | --- |
| Normal human | 20 | 1 |
| Colon cancer patient | 10 | 10 |
| Stomach cancer patient | 10 | 10 |
| Lymphosarcoma patient | 10 | 10 |

EXAMPLE 3

Figure 3:
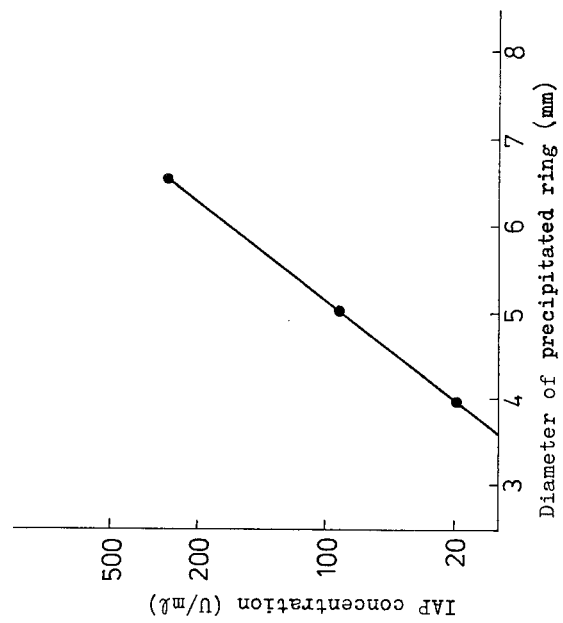
FIG. 3 shows the relationship between the diameter of the ring of precipitate and the quantity of IAP when IAP was quantitated with the specific immune serum prepared by the present invention.

Purified agar was added to 1/15 M phosphate buffered saline (pH=7.4) to make a 1.0% gel. The mixture was melted at 55° C. and the immune serum was added to make a final concentration of 3%. The mixture was poured into a container in such a way that a gel sheet with a flat surface and 1.0 to 1.5 mm in thickness was formed. Wells were formed as in the case of Example 2, and IAP reference solutions diluted to 1/1, 1/4 and 1/16 in concentration and sample (each exactly 5 μl) were measured into the wells in the gel sheet and left for 24 hours at room temperature. The diameters of the rings of precipitate were measured as shown in FIG. 3. It was confirmed that the quantity of IAP is a function of the diameter of the ring or band of precipitate.

What is claimed is:

1. A specific diagnostic immune serum for cancer diagnosis prepared by immunizing a non-human animal with an acid protein composition having immunosuppressive properties (IAP) having an isoelectric point pH of 2.9 to 3.3 determined by thin layer gel electrofocusing and a molecular weight of about 59,000 determined by electrophoresis with 2.5% polyacrylamide gel containing sodium dodecyl sulfate, said acid protein compositions being a white powder exhibiting the following properties:

decomposition point 265° C.

soluble in water and in 0.01 M phosphate buffered saline insoluble in methanol, ethanol, butanol, acetone, ethylacetate and chloroform positive color reaction with von Euler's reagent, Ehrlich's reagent, Buret's reagent and Molisch's reagent negative color reaction with ferric chloride reagent and Lieberman's reagent positive reaction to ninhydrin after hydrolysis in 6 N hydrolchloric acid at 120° C. for 15 hours infrared absorption spectrum with 0.5% K Br showing maxima at 3300 $cm^{-1}$, 2940 $cm^{-1}$, 2340 $cm^{-1}$, 1650 $cm^{-1}$, 1540 $cm^{-1}$, 1440 $cm^{-1}$, 1400 $cm^{-1}$, 1240 $cm^{-1}$, 1060 $cm^{-1}$, ultra-violet absorption spectrum of an 0.02% solution in distilled water λmax=280 nm and which is obtainable by negative ion-exchange chromatography from a human body liquid selected from the group consisting of serum, peritoneal fluid, thoracic fluid, urine and other body liquids of humans suffering from cancer and the liquid extracted from placentas of healthy humans.

2. A method for preparing a specific diagnostic immune serum for cancer diagnosis which comprises the steps of:

(a) preparing a solution in an aqueous injectable medium of an acid protein composition having immunosuppressive properties (IAP) having an isoelectric point pH of 2.9 to 3.3 determined by thin layer gel electrofocusing and a molecular weight of about 59,000 determined by electrophoresis with 7.5% polyacrylamide gel containing sodium dodecyl sulfate, said acid protein composition being a white powder exhibiting the following properties:

decomposition point 265° C.

soluble in water and in 0.01 M phosphate buffered saline insoluble in methanol, ethanol, butanol, acetone, ethylacetate and chloroform positive color reaction with von Euler's reagent, Ehrlich's reagent, Buret's reagent and Molisch's reagent negative color reaction with ferric chloride reagent and Lieberman's reagent positive reaction to ninhydrin after hydrolysis natant IAP antibody-containing liquid phase; and (i) separating the supernatant IAP anti-body-containing liquid from the sediment.

3. The process as defined in claim 2 which further comprises the step of:

(a) combining the IAP antibody-containing liquid separated in step (i) with fresh human serum to obtain a second IAP antibody-containing serum mixture;

(b) allowing a second sediment and a second IAP antibody-containing supernatant liquid to form in the second serum mixture; and (c) recovering the second supernatant IAP antibody-containing liquid.

4. A specific diagnostic immune serum for cancer diagnosis prepared by the process as defined in claim 1.

* * * * *